(12) United States Patent
Gagne et al.

(10) Patent No.: US 8,945,487 B2
(45) Date of Patent: Feb. 3, 2015

(54) SELF-SEALING SAMPLE COMPARTMENT FOR A LIQUID CHROMATOGRAPHY SYSTEM

(75) Inventors: Daniel J. Gagne, Smithfield, RI (US); Joshua A. Shreve, Franklin, MA (US); James E. Usowicz, Webster, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 13/519,706

(22) PCT Filed: Jan. 11, 2011

(86) PCT No.: PCT/US2011/020737
§ 371 (c)(1),
(2), (4) Date: Aug. 29, 2012

(87) PCT Pub. No.: WO2011/085340
PCT Pub. Date: Jul. 14, 2011

(65) Prior Publication Data
US 2013/0004388 A1    Jan. 3, 2013

Related U.S. Application Data

(60) Provisional application No. 61/293,927, filed on Jan. 11, 2010.

(51) Int. Cl.
| | | |
|---|---|---|
| *B01L 9/00* | (2006.01) | |
| *G01N 30/04* | (2006.01) | |
| *G01N 30/54* | (2006.01) | |
| *G01N 30/30* | (2006.01) | |

(Continued)

(52) U.S. Cl.
CPC .............. *G01N 30/04* (2013.01); *G01N 30/54* (2013.01); *G01N 2030/3084* (2013.01)
USPC ......................................... 422/566

(58) Field of Classification Search
USPC ................. 422/547, 549, 560, 565, 566, 567; 73/61.52, 61.55, 61.56
See application file for complete search history.

(56) References Cited

U.S. PATENT DOCUMENTS

| | | |
|---|---|---|
| 3,527,101 A | 9/1970 | Sprunger et al. |
| 4,335,620 A | 6/1982 | Adams |

(Continued)

FOREIGN PATENT DOCUMENTS

| | | |
|---|---|---|
| WO | 02/36708 A2 | 5/2002 |
| WO | 03/061453 A2 | 7/2003 |

OTHER PUBLICATIONS

International Search Report and Written Opinion for counterpart international application No. PCT/US2011/020737 dated Mar. 25, 2011; 7 pages.

(Continued)

*Primary Examiner* — Jill Warden
*Assistant Examiner* — Dwayne K Handy
(74) *Attorney, Agent, or Firm* — Schmeiser, Olsen & Watts LLP; William G. Guerin

(57) ABSTRACT

Described is a self-sealing thermal enclosure. In various embodiments, the self-sealing thermal enclosure includes an enclosure having a wall with an opening. The enclosure is configured to surround a temperature-controlled environment. The self-sealing thermal enclosure also includes a porous seal disposed adjacent to the wall at the opening. The porous seal is compressible and is fabricated from an open cell foam material. When the porous seal has absorbed a fluid such as a condensate, the temperature-controlled environment is sealed from an ambient environment such that the flow of air into or out of the enclosure is substantially reduced or eliminated.

15 Claims, 2 Drawing Sheets

(56) References Cited

U.S. PATENT DOCUMENTS

| | | |
|---|---|---|
| 6,352,266 B1 | 3/2002 | Rigoli |
| 2003/0087454 A1 | 5/2003 | Schultz et al. |
| 2003/0205515 A1 | 11/2003 | Purdom et al. |
| 2007/0166203 A1 | 7/2007 | Huang et al. |
| 2007/0224089 A1 | 9/2007 | Logan |

OTHER PUBLICATIONS

Extended European Search Report in related European patent application No. 11732293.3, mailed on Aug. 25, 2014; 4 pages.

SELF-SEALING SAMPLE COMPARTMENT FOR A LIQUID CHROMATOGRAPHY SYSTEM

RELATED APPLICATION

This application claims the benefit of the earlier filing date of U.S. Provisional Patent Application Ser. No. 61/293,927, filed Jan. 11, 2010 and titled "Liquid Chromatography System with a Self-Sealing Barrier for a Cooled Sample Chamber," the entirety of which is incorporated herein by reference.

FIELD OF THE INVENTION

The invention relates generally to sealing temperature controlled enclosures. More particularly, the invention relates to condensate control in a refrigerated sample manager for a liquid chromatography system.

BACKGROUND

High performance liquid chromatography (HPLC) and ultra performance liquid chromatography (UPLC) systems typical typically include a sample compartment that is adapted for receiving a number of sample vials or wells each containing a sample for analysis. Sample vials are arranged in one or more sample trays that can be loaded into and removed from the sample compartment by a user. Some systems include an auto-sampler that utilizes an automated process to control the position and movement of a sample needle within the sample compartment. For example, the sample needle may be moved to the location of a sample vial. The sample needle is then inserted into the sample vial to extract the sample and to subsequently inject the sample into a high pressure mobile phase.

The temperature of a sample can influence the results of liquid chromatography analysis; therefore it is desirable to maintain the sample compartment within a limited temperature range so that variations in the compartment temperature do not significantly affect measurement accuracy and repeatability. For example, the sample compartment may be cooled to a temperature below the ambient temperature using thermoelectric cooling. One or more fans generate an airflow that is directed across the cooling system and through the sample compartment.

Leakage from the compartment and infiltration of ambient air into the compartment can adversely affect thermal control. The compartment may be cooled relative to the ambient environment. Consequently, water or other forms of condensate can condense on cold surfaces that are exposed to the ambient environment.

SUMMARY OF THE INVENTION

In one aspect, the invention features a self-sealing thermal enclosure that includes an enclosure configured to surround a temperature-controlled environment. The enclosure has a wall with an opening. The self-sealing thermal enclosure also includes a porous seal disposed adjacent to the wall at the opening. The porous seal is compressible and includes an open cell foam material. The temperature-controlled environment is sealed from an ambient environment when the porous seal is compressed and has absorbed a fluid.

In another aspect, the invention features self-sealing sample compartment for a liquid chromatography system. The self-sealing sample compartment includes a thermally-insulated compartment, a structural member and a porous seal. The thermally-insulated compartment is configured to surround a temperature-controlled environment for a liquid chromatography sample and has a wall with an opening. The structural member is attached to the thermally-insulated compartment and has a portion exposed to the temperature-controlled environment and a portion exposed to an ambient environment external to the thermally-insulated compartment. The porous seal includes an open cell foam material and is disposed adjacent to the wall of the thermally-insulated compartment at the opening to receive a condensate formed on the portion of the structural member exposed to the ambient environment. The temperature-controlled environment is sealed from the ambient environment when the porous seal has absorbed a fluid

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview of various embodiments of a self-sealing thermal enclosure according to the invention, a porous barrier is disposed at an opening, or gap, on a wall of a thermally-insulated enclosure. The porous barrier reduces the flow of air into or out of the enclosure and is self-sealing when saturated with a fluid such as a condensate. The fluid is drawn into the porous material from the inside or outside of the enclosure. In some embodiments, the thermal enclosure is a sample compartment of a liquid chromatography system. The porous seal avoids the need to provide a pathway for condensate to escape the compartment and, in some embodiments, eliminates the need for a drip tray outside of the compartment. In addition, air flow into and out from the compartment is substantially reduced or eliminated, resulting in better thermal control of the compartment while preventing the condensate from adversely affecting external components located near the compartment.

Figure 1:
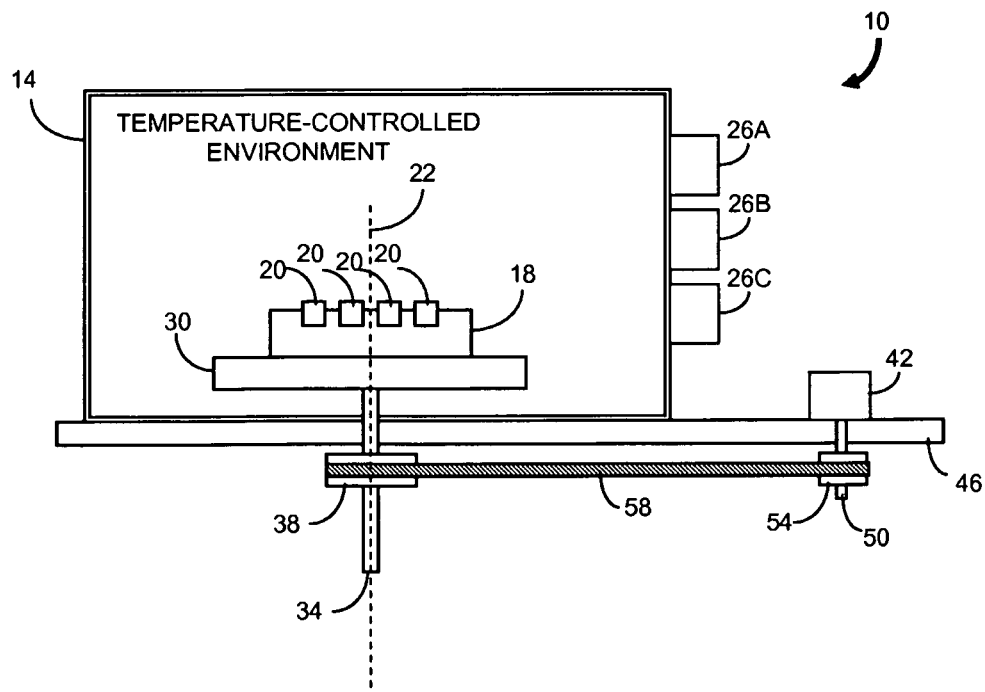
FIG. 1 is a block diagram of a portion of a liquid chromatography system that includes a self-sealing sample compartment according to an embodiment of the invention.

FIG. 1 is a block diagram of a portion of a liquid chromatography system 10, including a sample compartment, or sample chamber, 14 according to an embodiment of the invention. As used herein, a sample compartment means an enclosure or housing with an enclosed temperature-controlled volume in which a number of sample vials or wells are maintained. The illustrated sample compartment 14 includes a removable sample tray 18 that rotates about a vertical axis 22. A sample needle (not shown) is controlled by a translation mechanism that allows for a sample in one of the sample vials 20 held in the sample tray 18 to be injected into the mobile phase of the liquid chromatography system for analysis. The translation mechanism employs three hybrid step motors 26A, 26B and 26C (generally 26) that are secured to a wall of the sample compartment 14 and are exposed to the ambient environment. Each motor 26 includes a motor shaft (not shown) that can extend into the sample compartment 14. The motor shafts cooperate with components inside the sample compartment 14 to provide vertical and radial translational motion of the sample needle.

A rotary drive mechanism is used to affect rotation of the sample tray 18. The rotary drive mechanism includes a mounting platform 30 to receive the sample tray 18, a tray shaft 34 and a pulley 38. The tray shaft 34 has an upper portion disposed inside the sample compartment 14 and a lower portion disposed outside the sample compartment 14. The mounting platform 30 is secured to the upper portion of the tray shaft 34. A motor 42 is mounted to a system base plate, or datum plate, 46 and is coupled via a motor shaft 50, drive pulley 54 and drive belt 58 to the tray shaft pulley 38. Thus rotation of the motor shaft 46 results in rotation of the sample tray 18. The translation mechanism and rotary drive mechanism operate in a coordinated manner to enable the injection needle to be moved to the location of any sample vial 20 in the sample tray 18.

Figure 2:
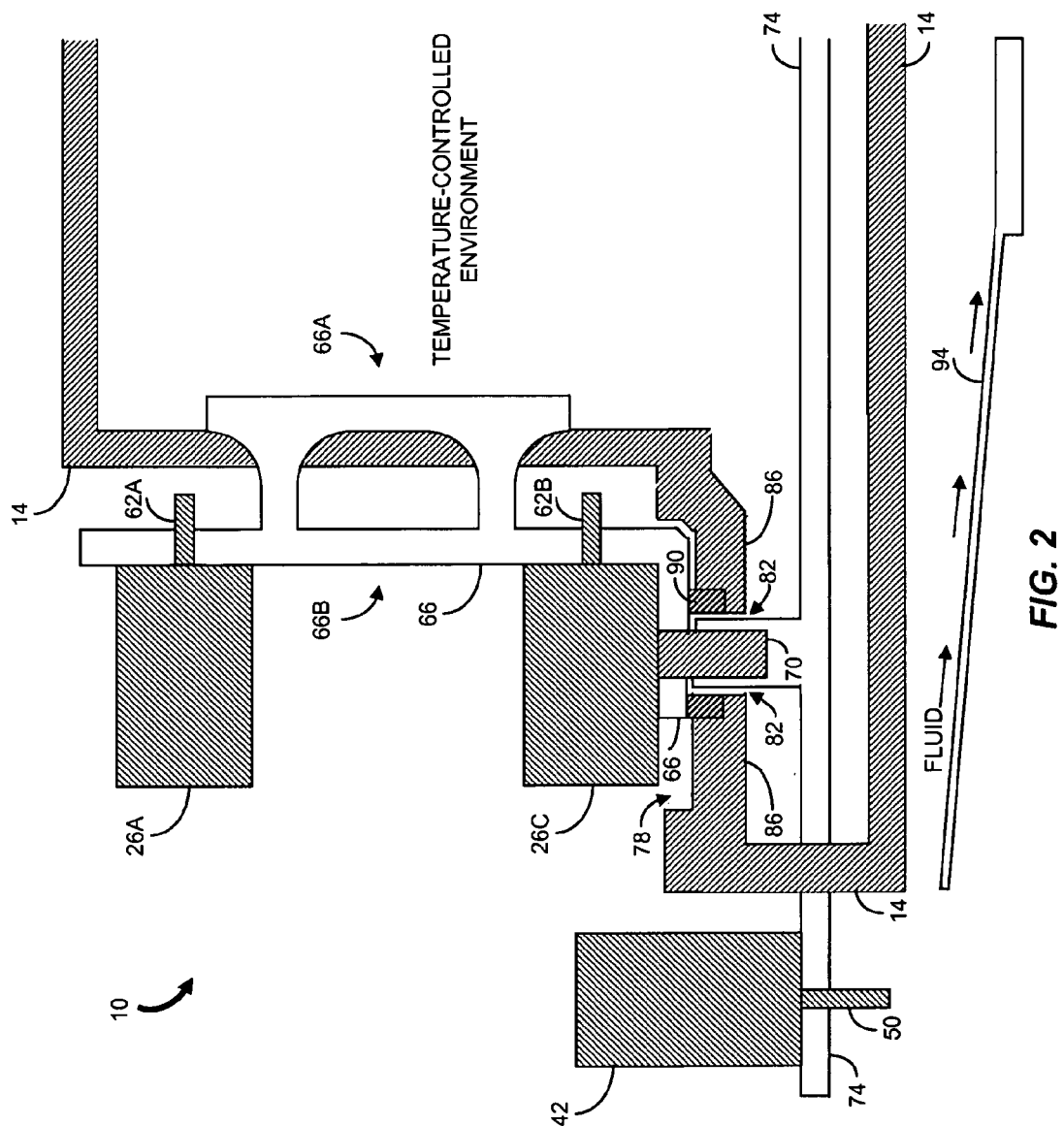
FIG. 2 is an illustration of a portion of a liquid chromatography system corresponding to the portion shown in FIG. 1.

FIG. 2 is a cross-sectional illustration of the portion of the liquid chromatography system 10 shown in FIG. 1 with some elements removed for clarity of the remaining structure and components. In this view, only two of the motors 26A and 26C, with motor shafts 62A and 62B, respectively, are visible. Referring to FIG. 1 and FIG. 2, the motors 26 are secured to a wall of the compartment 14 using a structural member such as a mounting bracket 66. An internal bracket portion 66A resides inside the compartment 14 and is exposed to the lower temperature of the enclosed environment. An external bracket portion 66B resides outside the compartment 14 and is exposed to the higher temperature of the ambient environment. The lower motor 26C is maintained in a desired position by a pin 70 located in a feature extending from a datum plate 74. The motor 42 used to control rotation of the sample tray 18 is mounted to a rigid structure, shown in FIG. 2 as the datum plate 74, on a region that is exposed to the ambient environment.

During periods of operation when the temperature of the temperature-controlled environment inside the sample compartment 14 is lower than the ambient temperature, the temperature of the bracket 66 is typically less than the temperature of the ambient environment. Consequently, condensation can form on the external bracket portion 66B and flow downward. In the illustrated system 10, the condensation can collect in a recessed region 78 below the lower motor 26C. With sufficient time, the condensation can collect sufficiently such that overflow from the recessed region 78 spills over and adversely affects operation of other system components. For example, overflow can adversely affect operation of the motor 42 used to rotate the sample tray 18.

The sample compartment 14 includes a gap 82 between region of the datum plate 74 that receives the pin 70 and the adjacent wall 86 of the sample compartment 14. A porous seal 90 is compressed in a position between the bracket 66 and adjacent wall 86. In some embodiments, the components in contact with the porous seal 90 are fabricated from materials that resist corrosion or that are otherwise treated according to anti-corrosion processes.

Figure 3:
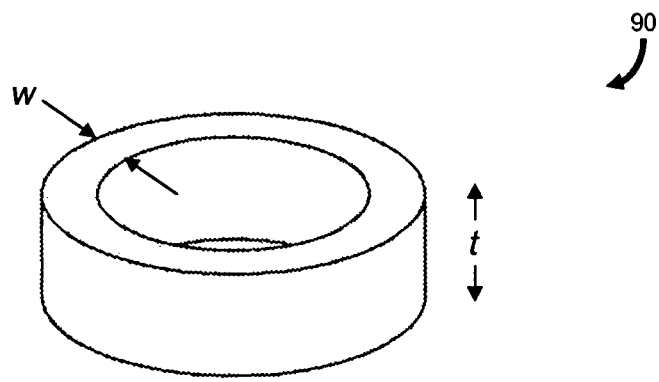
FIG. 3 is a porous seal that can be used to self-seal the sample compartment shown in FIG. 2.

The porous seal 90 is in the form of a gasket as shown in FIG. 3. The gasket is fabricated from an open cell foam that absorbs fluid. In a preferred embodiment, the gasket is formed from low density ethylene propylene diene monomer (EPDM) open cell foam available, for example, from Stockwell Elastomerics, Inc. of Philadelphia, Pa. In one embodiment, the gasket has an inner diameter of approximately 1.03 inch, a wall thickness w of approximately 0.42 inch and a thickness t of approximately 0.38 inch.

Referring again to FIG. 2, as the condensate begins to flow downward from the bracket 66, the porous seal 90 wicks the condensate from the recessed region 78. After the seal 90 becomes saturated, the condensate flows through the seal 90 into the sample compartment 14 and is directed to a fluid management system such as a drip tray 94 as is known in the art. In one embodiment, the condensate entering the sample compartment 14 through the seal 90 drips directly into the drip tray 94. Alternatively, the condensate may flow from the seal 90 along internal structural features to the drip tray 94.

As the porous seal 90 absorbs moisture, a substantially airtight seal is formed between the ambient environment and the temperature-controlled environment inside the sample compartment 14. Thus undesirable infiltrate is prevented and temperature management is improved. Advantageously, the porous seal 90 can be used in place of an external drip tray for the purposes of attracting and redirecting condensation or other liquid buildup to an area where fluid management can more conveniently be implemented. This is particularly useful for condensation in areas where drip trays cannot be positioned. The total system cost may be reduced due to a less complex drip tray or fluid management design. Moreover, the porous seal 90 can prevent the occurrence of fluid dripping on system components that are adversely affected by moisture.

Although embodiments of a self-sealing sample compartment of a particular configuration are described above, the invention further contemplates a wide variety of structural configurations in which condensate collection or other fluid buildup can be managed according to the use of one or more porous seals while maintaining a substantially sealed environment. For example, a porous seal may be formed as a gasket and positioned to fill or seal an opening at a different location in an enclosure wall. In another embodiment, the porous seal is a layer of material that is located over a larger opening. The layer acts as a drainage boundary that limits the passage of air while allowing fluid to flow through the layer.

In other embodiments, a self-sealing enclosure includes a thermally-insulated enclosure configured to surround a temperature-controlled environment. The enclosure includes at least one wall having an opening between the internal temperature-controlled environment and the external, or ambient, environment. A porous seal is disposed at the opening and may be secured in place by compression between two or more surfaces or various means of attachment. The porous seal is formed from an open cell foam material. The temperature-controlled environment is sealed from the ambient environment when the porous seal has absorbed a fluid. The porous seal can become saturated and conduct the fluid in either direction between the internal and ambient environments while maintaining a seal to prevent the inflow or outflow of air.

While the invention has been shown and described with reference to specific embodiments, it should be understood by those skilled in the art that various changes in form and detail may be made therein without departing from the spirit and scope of the invention as recited in the accompanying claims.

What is claimed is:

1. A self-sealing thermal enclosure, comprising:
   an enclosure configured to surround a temperature-controlled environment, the enclosure having a wall separating the temperature-controlled environment from an ambient environment, the wall having an opening therein; and
   an absorbent porous seal compressed against the wall at the opening, the absorbent porous seal comprising an open cell foam material, wherein a flow of air between the temperature-controlled environment and the ambient environment through the opening is reduced when the absorbent porous seal has absorbed a liquid and wherein liquid is conducted through the opening when the absorbent porous seal is saturated with the liquid.

2. The self-sealing thermal enclosure of claim 1 wherein the enclosure is thermally insulated.

3. The self-sealing thermal enclosure of claim 1 wherein the enclosure comprises a sample compartment for a liquid chromatography system.

4. The self-sealing thermal enclosure of claim 1 wherein the open cell foam material is a synthetic rubber.

5. The self-sealing thermal enclosure of claim 4 wherein the synthetic rubber is ethylene propylene diene monomer (EPDM).

6. The self-sealing thermal enclosure of claim 1 wherein the absorbent porous seal is a gasket.

7. The self-sealing thermal enclosure of claim 1 wherein the absorbent porous seal is shaped to direct a fluid to a fluid management system.

8. The self-sealing thermal enclosure of claim 7 further comprising the fluid management system.

9. A self-sealing sample compartment for a liquid chromatography system, comprising:
   a thermally-insulated compartment configured to surround a temperature-controlled environment for a liquid chromatography sample, the thermally-insulated compartment having a wall separating the temperature-controlled environment from an ambient environment, the wall having an opening therein;
   a structural member attached to the thermally-insulated compartment and having a portion exposed to the temperature-controlled environment and a portion exposed to the ambient environment; and
   an absorbent porous seal compressed against the wall of the thermally-insulated compartment at the opening to receive a condensate formed on the portion of the structural member exposed to the ambient environment, the absorbent porous seal comprising an open cell foam material that absorbs the condensate, wherein a flow of air between the temperature-controlled environment and the ambient environment through the opening is reduced when the absorbent porous seal has absorbed the condensate and wherein the condensate is conducted through the opening when the absorbent porous seal is saturated with the condensate.

10. The self-sealing sample compartment of claim 9 wherein the open cell foam material is a synthetic rubber.

11. The self-sealing sample compartment of claim 10 wherein the synthetic rubber is ethylene propylene diene monomer (EPDM).

12. The self-sealing sample compartment of claim 9 wherein the absorbent porous seal is a gasket.

13. The self-sealing sample compartment of claim 9 wherein the absorbent porous seal is shaped to direct the condensate to a fluid management system.

14. The self-sealing sample compartment of claim 13 further comprising the fluid management system.

15. The self-sealing sample compartment of claim 14 wherein the fluid management system is a drip tray.

* * * * *